US008604819B2

(12) United States Patent
Shimotomai et al.

(10) Patent No.: US 8,604,819 B2
(45) Date of Patent: Dec. 10, 2013

(54) INSPECTING APPARATUS FOR PHOTOVOLTAIC DEVICES

(75) Inventors: Mitsuhiro Shimotomai, Tokyo (JP); Hikaru Ichimura, Tokyo (JP)

(73) Assignee: Nisshinbo Holdings Inc., Tokyo (JP)

( * ) Notice: Subject to any disclaimer, the term of this patent is extended or adjusted under 35 U.S.C. 154(b) by 401 days.

(21) Appl. No.: 13/061,496

(22) PCT Filed: Aug. 26, 2009

(86) PCT No.: PCT/JP2009/065281
§ 371 (c)(1),
(2), (4) Date: Feb. 28, 2011

(87) PCT Pub. No.: WO2010/024452
PCT Pub. Date: Mar. 4, 2010

(65) Prior Publication Data
US 2011/0148453 A1    Jun. 23, 2011

(30) Foreign Application Priority Data

Aug. 28, 2008  (JP) .................................. 2008-218927

(51) Int. Cl.
*G01R 31/26*  (2006.01)
(52) U.S. Cl.
USPC .................................................... 324/761.01
(58) Field of Classification Search
None
See application file for complete search history.

(56) References Cited

U.S. PATENT DOCUMENTS 7,528,615 B2 *    5/2009   Shimotomai ............ 324/754.23

FOREIGN PATENT DOCUMENTS

| JP | 2002-148094 | 5/2002 |
| JP | 2006-90990 | 4/2006 |
| JP | 2007-88419 | 4/2007 |
| JP | U3141553 | 4/2008 |
| JP | U3143169 | 6/2008 |
| JP | P4153021 | 7/2008 |
| WO | 2006/059615 | 6/2006 |

* cited by examiner

*Primary Examiner* — Minh N Tang
(74) *Attorney, Agent, or Firm* — J.C. Patents

(57) ABSTRACT

Provided is an inspecting apparatus for inspecting a photovoltaic devices by applying a current to the photovoltaic devices in a forward direction to make the photovoltaic devices emit EL light which is simple in structure and capable of shortening inspection time in inspecting a defect from a photographed image with a perfect resolution. The inspecting apparatus includes a darkroom (110) provided with an upper surface (111) having an opening portion (112), a support device provided at the upper surface of the darkroom (110) to support the photovoltaic devices as an inspecting object (200) on the opening portion (112), cameras (121, 122 and 123) disposed inside the darkroom (110) for photographing the inspecting object (200), and a moving device configured to move the cameras in the darkroom (110). The moving device includes an x-axial guiding portion (140), a motor (142) and a timing belt (144).

8 Claims, 7 Drawing Sheets

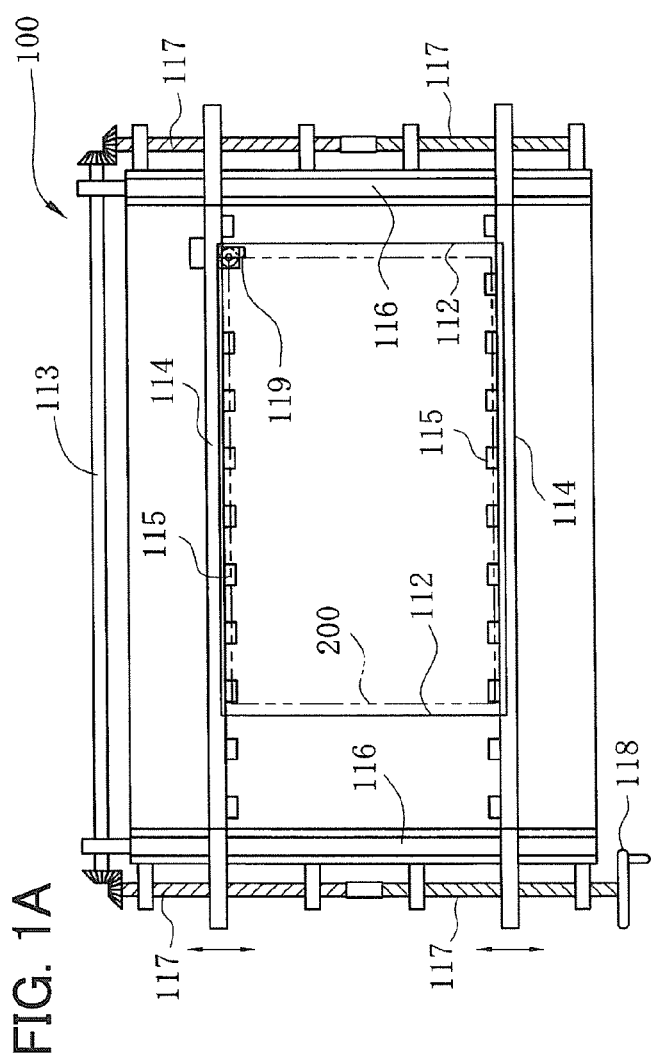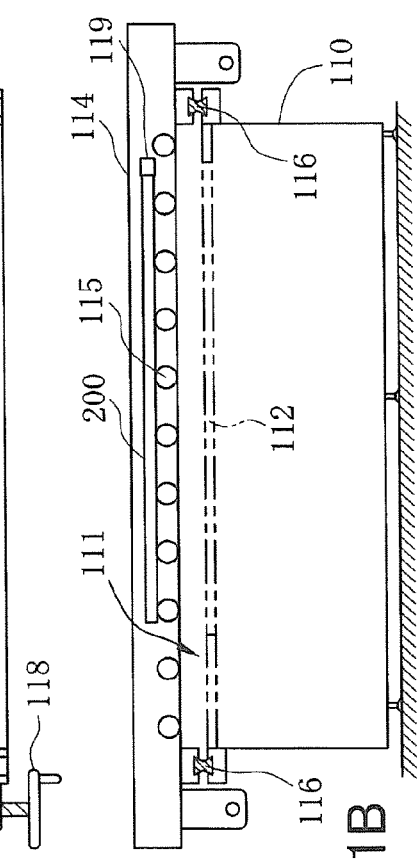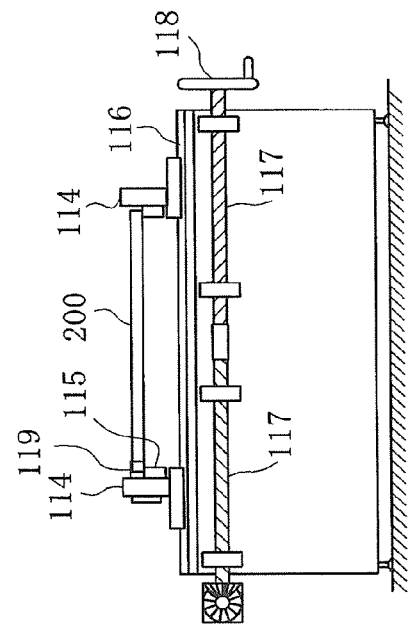

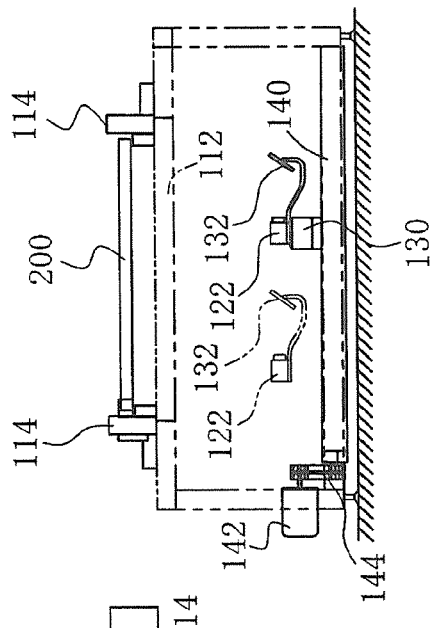
FIG. 3C
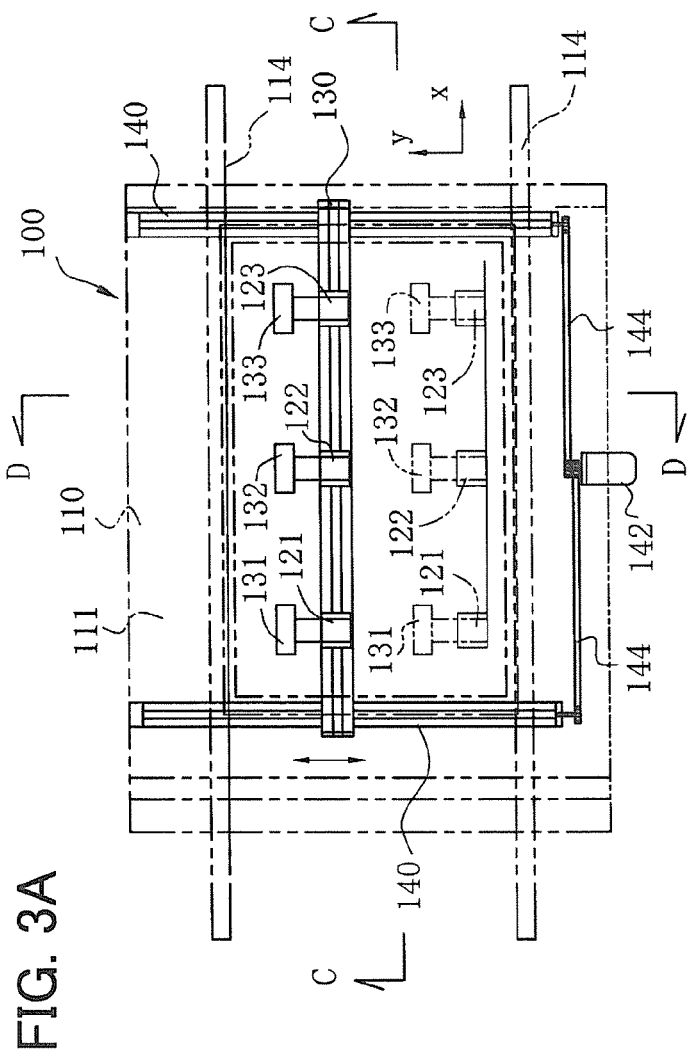
FIG. 3A
FIG. 3B

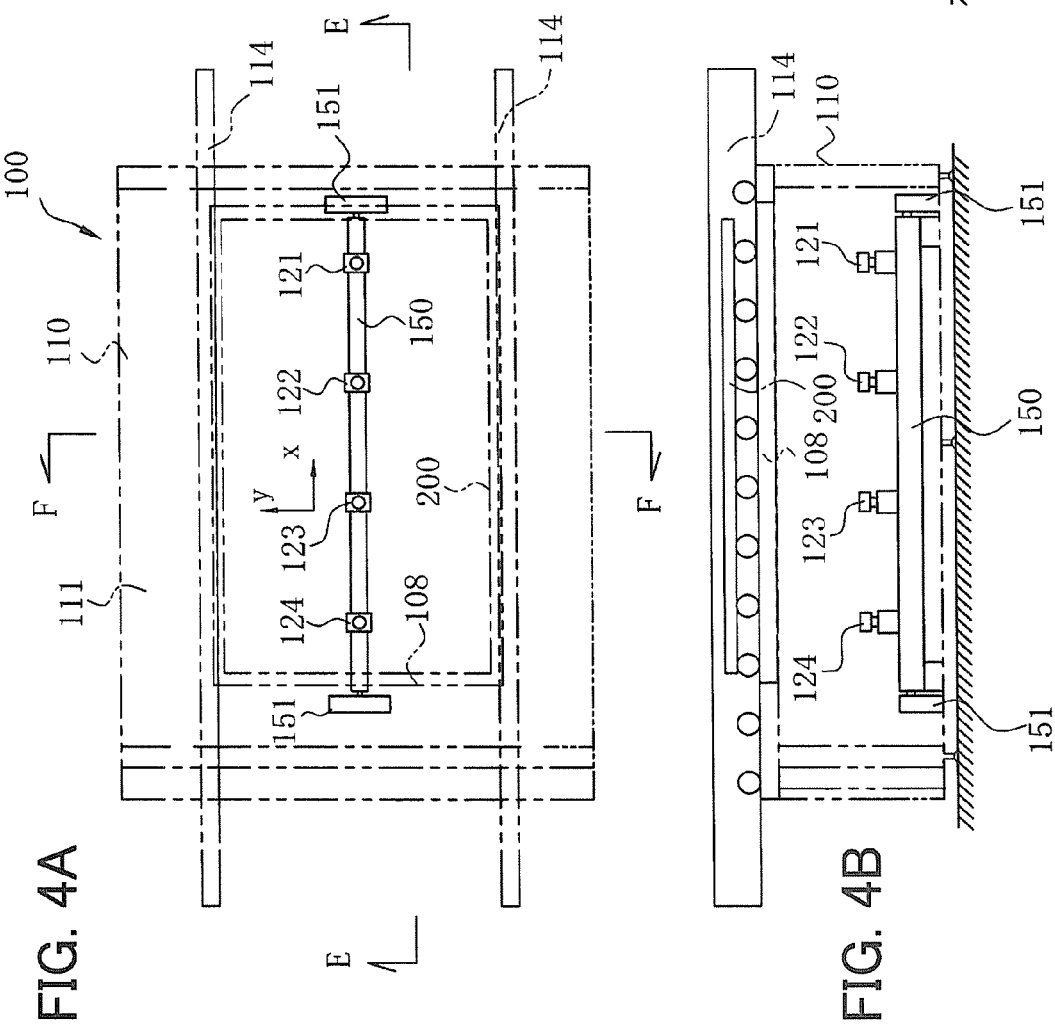

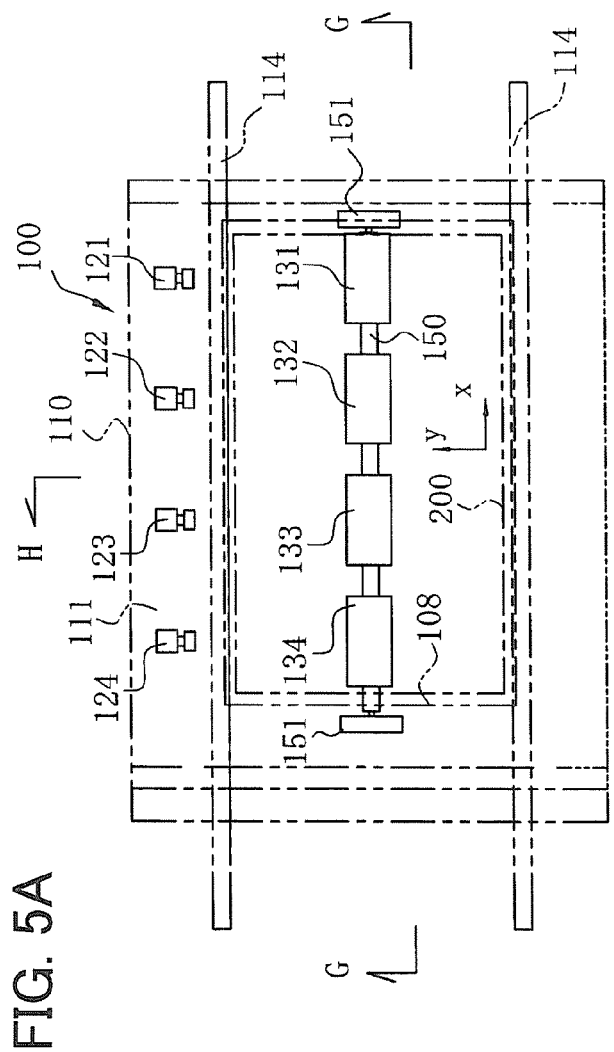
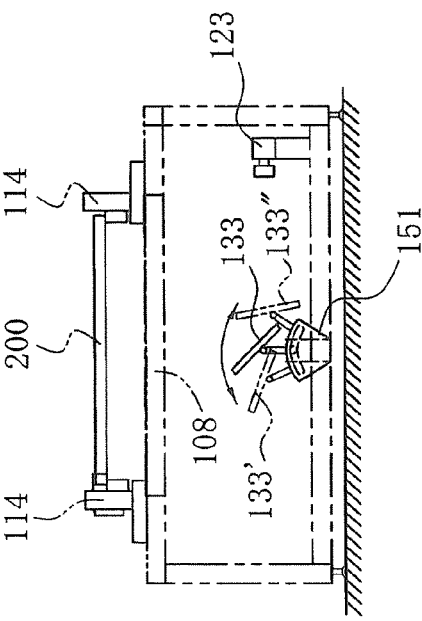
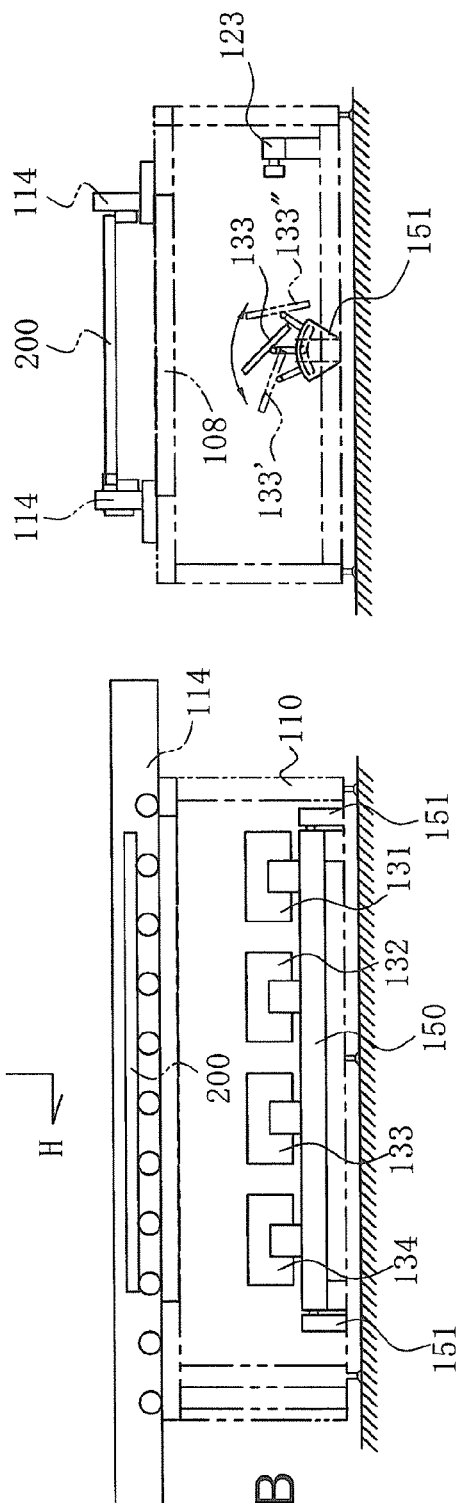

RELATED ART

INSPECTING APPARATUS FOR PHOTOVOLTAIC DEVICES

CLAIM FOR PRIORITY

The present application is a U.S. National Stage of Application No. PCT/JP2009/065281, filed on Aug. 26, 2009, and claims priority from Japanese patent application no. 2008-218927 (filed on Aug. 28, 2008). The entire contents of the aforementioned application are hereby incorporated by reference herein.

BACKGROUND OF THE INVENTION

1. Field of the Invention

The present invention relates to an inspecting apparatus which is employed to inspect general performance of a photovoltaic devices, such as a photovoltaic cell, a photovoltaic devices string which is formed by connecting the photovoltaic cells in series, a photovoltaic devices panel which is formed by disposing a plurality of photovoltaic strings in parallel, and the like.

2. Description of the Background Art

It is well known that a silicon photovoltaic devices is employed to harness solar energy. In the manufacture of the photovoltaic devices, it is important to evaluate whether the photovoltaic devices has predetermined power generation capacity. The evaluation is usually performed by measuring output characteristics thereof.

The output characteristics are the photovoltaic conversion characteristics obtained by measuring current-voltage characteristics of the photovoltaic devices under light irradiation. As a light source, it is desired to use the solar light. However, since the intensity of the solar light varies in relation to weather, a solar simulator is employed. In the solar simulator, a xenon lamp, a metal halide lamp or the like is employed as an alternative to the solar light. If the aforementioned light source has been lighted for a long time, the temperature thereof rises or the like, leading to a variation on the light intensity thereof. Therefore, by using the flash light of the aforementioned light source, it is able to plot the output characteristic curve of the photovoltaic devices on the basis of collected data by setting a voltage as the lateral axis and a current as the vertical axis (for example, refer to Japanese Patent Application Laid-Open No. 2007-88419).

The following method different from the solar simulator is disclosed in the Patent Document WO/2006/059615. By applying a voltage to a polycrystalline silicon photovoltaic devices element in a forward direction, the photovoltaic devices element emits an electro-luminescence (hereinafter, referred to as "EL") light. The same occurs in a thin-film typed photovoltaic devices. By studying the EL light emitted from the photovoltaic devices element, it is able to obtain the distribution of current density of the photovoltaic devices element. The defect of the photovoltaic devices element can be determined on the basis of the uneven distribution of current density. Namely, a portion which emits no EL light is determined to be a defective portion, and the photovoltaic devices element is determined to have the predetermined power generation capacity if the total area of the defective portions is smaller than a predetermined amount.

The structure of an inspecting apparatus described in the Patent Document WO/2006/059615 is schematically illustrated in FIG. 7. The inspecting apparatus 10 includes a darkroom 11, a CCD camera 12 which is disposed at an upper portion of the darkroom 11, a power source 14 which applies a current to a photovoltaic cell 13 disposed on the floor of the darkroom 11, and an image processing apparatus 15 which processes image signals from the CCD camera 12.

The darkroom 11 is provided with a window 11a where a finder 12a of the CCD camera 12 is disposed. Therefore, an image to be photographed by the CCD camera 12 can be confirmed by watching with an eye from the finder 12a. As the image processing apparatus 15, a computer is employed.

In the inspecting apparatus 10 illustrated in FIG. 9, the photovoltaic cell 13 is disposed at a lower position and is photographed by the camera from an upper position. However, since the EL light emitted from the photovoltaic cell 13 is a weak light ray of wavelength between 1,000 nm and 1,300 nm, it is not able to be detected unless the photovoltaic cell is disposed inside the darkroom 11. In case that the inspecting object is a piece of photovoltaic cell, the dimension thereof is about 100 nm×100 nm, and the darkroom 11 in which the photovoltaic cell is disposed is small sized.

However, in case that the inspecting object is a photovoltaic devices panel, the dimension thereof is about 2 m×1 m; therefore, the darkroom 11 has to have a dimension capable of housing the photovoltaic devices panel. Further, the photovoltaic devices panel as the inspecting object has to be disposed inside the darkroom so as to be photographed by the CCD camera 12; therefore, a door has to be disposed in the darkroom for transporting the photovoltaic devices panel into or carrying out from the darkroom. If the inspecting apparatus is configured so as to transport the inspecting object into the darkroom, shading effect has to be secured when the disposed door is closed. It is also necessary that the inspecting apparatus is provided with a positioning member and a guide member for transporting the photovoltaic devices in the darkroom. Furthermore, it is also necessary to dispose an electrifying means in the darkroom for applying a current to the photovoltaic devices. Thereby, the inspecting apparatus becomes complicated in structure and expensive in price.

To photograph a large photovoltaic devices panel with one camera, the distance from the camera to the photovoltaic devices panel has to be kept greater, which makes the darkroom become large sized. By moving the camera to photograph the photovoltaic devices panel part by part for several times, the distance from the camera to the photovoltaic devices panel can be kept smaller, making the darkroom become small sized; however, the inspection time become longer. In order to shorten the inspection time by reducing the photographing times, the area of the photovoltaic devices panel to be photographed in one image will become greater; consequently, the resolution of the photographed image will become lower, and therefore it is impossible to inspect the defect accurately.

SUMMARY OF THE INVENTION

The present invention has been accomplished in view of the aforementioned problems, and an objective of the present invention is to provide an inspecting apparatus for inspecting a photovoltaic devices by applying a current to the photovoltaic devices in a forward direction to make the photovoltaic devices emit EL light which is simple in structure and capable of shortening inspection time in inspecting a defect from a photographed image with a perfect resolution.

To attain the objective described above, an inspecting apparatus for a photovoltaic devices of the present invention includes: a darkroom provided with an upper surface having an opening portion; a support means provided at the upper surface of the darkroom to support the photovoltaic devices as an inspecting object on the opening portion; and a plurality of cameras disposed inside the darkroom to photograph the inspecting object, the entire photovoltaic devices is photographed by each camera photographing an allocated part of the photovoltaic devices.

It is acceptable that a moving means is provided in the darkroom to move the plurality of cameras. It is also acceptable that the moving means includes a support member for fixing the plurality of cameras and the moving means reciprocates the support member linearly. It is also acceptable that each of the plurality of cameras is provided with a reflective plate to photograph the allocated part. The moving means may be configured to move the reflective plate together with the camera. Further, it is acceptable that a rock means is provided in the darkroom to rock each of the plurality of cameras for photographing the allocated part.

It is acceptable that each of the plurality of cameras is provided with a reflective plate to photograph the allocated part and a rocking means for rocking the reflective plate. Furthermore, it is acceptable that the opening portion is obturated by a transparent plate.

To inspect a photovoltaic devices with the inspecting apparatus of the present invention, firstly, the photovoltaic devices as the inspecting object is supported on the opening portion disposed at the upper surface of the darkroom. By applying a current to the photovoltaic devices, each photovoltaic cell constituting the photovoltaic devices emits the EL light. The emitting state of the EL light is photographed by the plurality of cameras, and analyzed by an image processing apparatus connected to the cameras, it is possible to determine whether the photovoltaic devices has a defect or not.

The photovoltaic devices can be inspected by disposing it on the upper surface of the darkroom from the outside of the darkroom; therefore, it is not necessary to provide a door for transporting the photovoltaic devices as the inspecting object into or carrying out of the darkroom. Accordingly, it is possible to simplify the structure of the darkroom, thereby, enabling miniaturization thereof.

Since the photovoltaic devices is allocated into parts and the plurality of cameras are employed to photograph respectively only the allocated parts, it is possible to inspect a defect from a photographed image with a perfect resolution at a short time. Further, since the area of the photographing subject is small, the distance between the camera and the photovoltaic devices can be made small; accordingly, the darkroom can be made small in size and cheap in price. The moving means includes a support member for fixing the plurality of cameras, and the moving means reciprocates the support member linearly; it is possible to move the plurality of cameras at the same speed in the same direction simultaneously, thereby, it is only necessary to manufacture a single moving means, which is cheap in price.

Further, incase that the inspecting object is a photovoltaic devices panel, the photovoltaic devices panel is transported in a manufacturing line (manufacturing apparatus, such as a laminating apparatus) with a light receiving surface thereof facing downward. The inspecting apparatus of the present invention is configured to have the opening portion disposed at the upper surface of the darkroom; accordingly, it is possible to dispose the photovoltaic devices panel on the inspecting apparatus without inversing it. Furthermore, by disposing the reflective plate oblique to the opening portion and photographing the image reflected in the reflective plate with the camera, the darkroom can be made further small. By photographing the photovoltaic devices panel with the plurality of cameras, it is possible to shorten inspection time in inspecting a defect from a photographed image with a perfect resolution; thereby, even the inspecting apparatus of the present invention is employed in a manufacturing line for the photovoltaic devices panel, it is possible to reduce the total manufacturing time in inspecting a defect at perfect accuracy.

Other features and advantages of the present invention will be apparent from the following description when taken in conjunction with the accompanying drawings, in which like reference characters designate similar or identical parts throughout the several views thereof.

BRIEF DESCRIPTION OF THE DRAWINGS

FIG. 1A is a planar view illustrating an inspecting apparatus for a photovoltaic devices according to the present invention;

FIG. 1B is a front view of FIG. 1A;

FIG. 1C is a right-side view of FIG. 1A;

FIG. 3A is a planar view illustrating an embodiment of the present invention where a darkroom is further miniaturized;

FIG. 3B is a sectional view along C-C line in FIG. 3A;

FIG. 3C is a sectional view from the right side along D-D line in FIG. 3A;

FIG. 4A is a planar view illustrating an embodiment of rocking the camera as a moving means;

FIG. 4B is a sectional view along E-E line in FIG. 4A;

FIG. 4C is a sectional view from the right side along F-F line of FIG. 4A;

FIG. 4D is a planar view illustrating allocated parts for each camera in photographing the inspecting object;

FIG. 5A is a planar view illustrating an embodiment where only a reflective plate is rocked;

FIG. 5B is a sectional view along G-G line in FIG. 5A;

FIG. 5C is a sectional view from the right side along H-H line in FIG. 5A;

DETAILED DESCRIPTION OF THE PREFERRED EMBODIMENTS

Hereinafter, an embodiment according to the present invention will be described in detail with reference to the drawings. In so doing, specific terminology is employed solely for the sake of clarity, and the present disclosure is not to be limited to the specific terminology so selected. It is to be understood that each specific element includes all technical equivalents that operate in a similar manner and achieve a similar result.

1. Inspecting Object: Photovoltaic Module

Figure 6A:
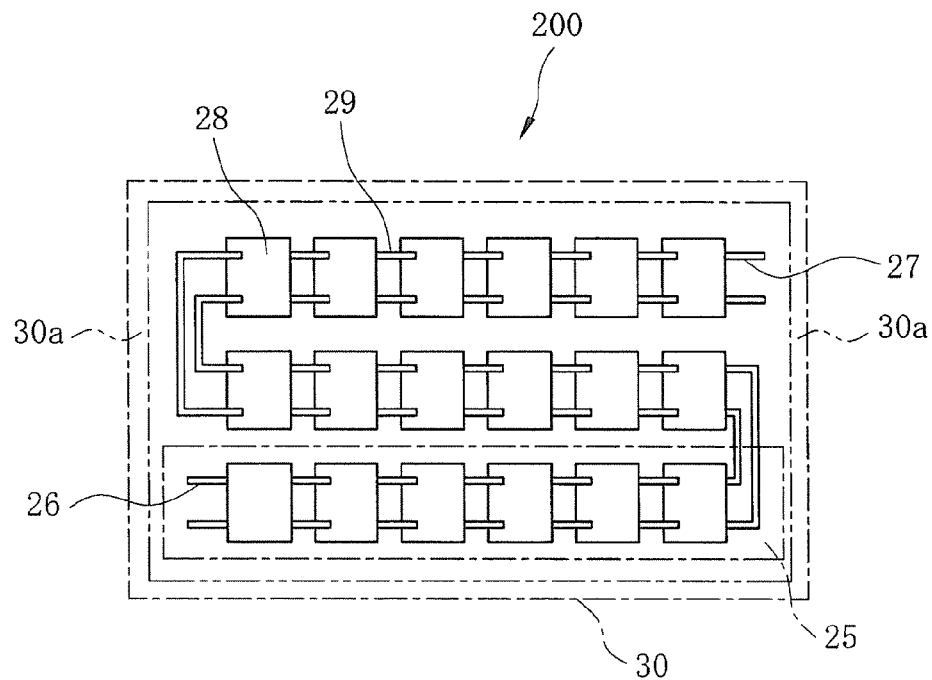
FIG. 6A is a planar view illustrating a configuration of the photovoltaic devices inspected by the inspecting apparatus of the present invention.
Figure 6B:
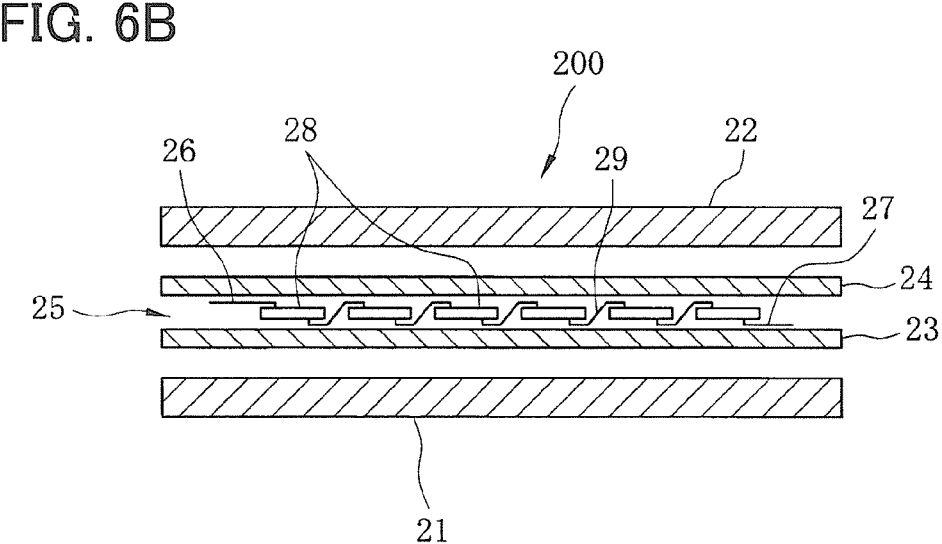
FIG. 6B is a sectional view thereof.

First, description is given on an example of an inspecting object 200 which is inspected by an inspecting apparatus of the present invention. FIG. 6A is a planar view explaining a configuration of a photovoltaic devices being inspected by the inspecting apparatus of the present invention; FIG. 6B is a sectional view thereof. In FIG. 6A, photovoltaic cells in the photovoltaic devices are clearly illustrated.

As illustrated by the planar view in FIG. 6A, the photovoltaic module as the inspecting object 200 is formed in the following way:

Plural square photovoltaic cells 28 are connected in series by lead wires 29 to form a string 25; thereafter, plural columns of strings 25 are connected by the lead wires 29 to form the photovoltaic module.

The photovoltaic devices as the inspecting object 200 may be formed from a single photovoltaic cell 28 only, or may be formed from the string 25 in which the plural photovoltaic cells 28 are connected linearly, or may be a photovoltaic devices panel 30 in which the plural columns of strings 25 are disposed in parallel and the photovoltaic cells 28 are disposed in matrix. As illustrated, the periphery of the photovoltaic devices panel 30 is provided with a margin 30a which can not be used as a light-receiving surface of the photovoltaic cell 28 or the like.

As illustrated in FIG. 6B, the configuration of the inspecting object 200 in sectional view is formed by disposing the plural columns of string 25 sandwiched by filling members 23 and 24 between a back surface member 22 disposed in an upper side and a transparent cover glass 21 disposed in a lower side.

The back surface member 22 is made of, for example, polyethylene resin or the like. The filling members 23 and 24 are made of, for example, EVA resin (polyethylene vinyl acetate resin). As described above, the string 25 is formed by connecting the photovoltaic cells 28 with the lead wires 29 between electrodes 26 and 27.

The photovoltaic module is obtained by piling the aforementioned constituent members and laminating with pressure under heating in vacuum to cross-link the EVA resin with a laminator or the like.

In addition, a photovoltaic devices, which is generally called as a thin film-type, may be employed as the inspecting object 200.

For example, a typical structure of this thin film-type photovoltaic devices is obtained in the following way:

depositing a power generating element comprised of a transparent electrode, a semiconductor and a back electrode via vacuum evaporation on a transparent cover glass disposed at the lower side; disposing the transparent cover glass at the lower side; covering the photovoltaic devices elements disposed on the glass with the filling members; covering the filling members with the back surface member; and laminating the piled constituet members with a laminator.

This kind of the thin film-type photovoltaic module as the inspecting object 200 only replaces crystalline cells with the aforementioned power generating elements, and the basic sealing structure is identical to the case of the crystalline cells in the aforementioned description.

2. Entire Configuration of the Inspecting Apparatus

Figure 2D:
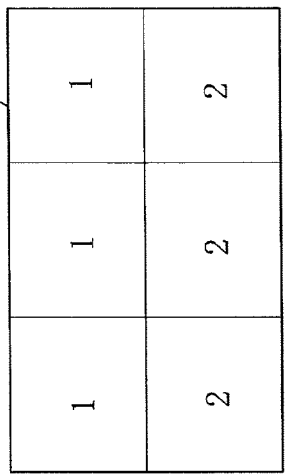
FIG. 2D is a planar view illustrating allocated parts for each camera in photographing an inspecting object.
Figure 2C:
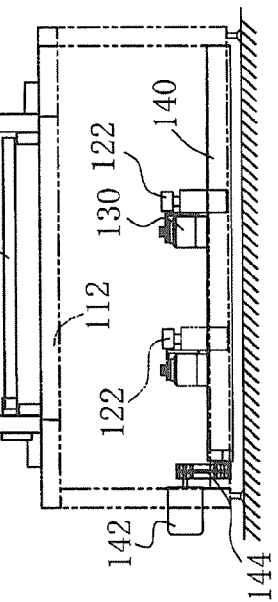
FIG. 2C is a sectional view from the right side along B-B line of FIG. 2A.
Figure 2A:
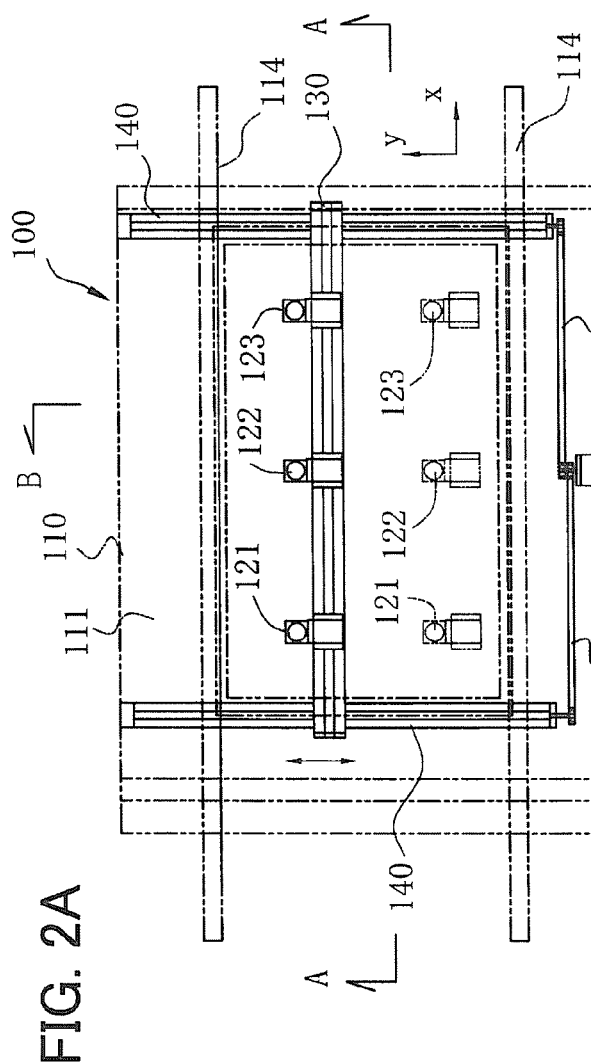
FIG. 2A is a planar view illustrating a configuration of a camera and a moving means of the inspecting apparatus for the photovoltaic devices according to the present invention.
Figure 2B:
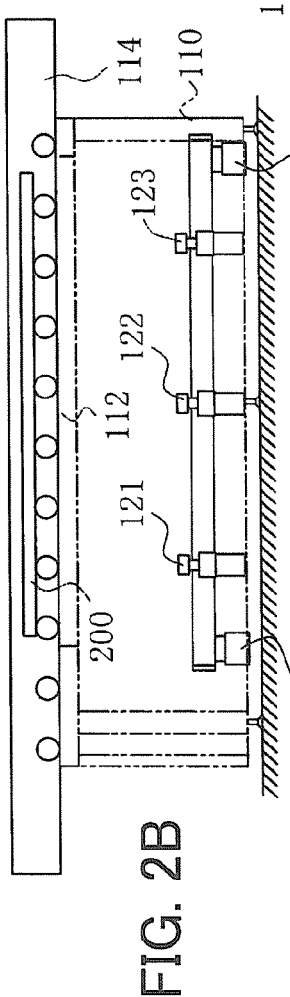
FIG. 2B is a sectional view along A-A line of FIG. 2A.

FIG. 1A is a planar view illustrating the inspecting apparatus of the present invention; FIG. 1B is a front view thereof; and FIG. 1C is a right-side view thereof. FIG. 2A is a planar view illustrating a configuration of a camera and a drive mechanism for the camera of the inspecting apparatus for the photovoltaic devices according to the present invention; FIG. 2B is a sectional view along A-A line of FIG. 2A; FIG. 2C is a sectional view from the right side along B-B line in FIG. 2A; FIG. 2D is a planar view illustrating allocated parts for each camera in photographing the inspecting object.

The inspecting apparatus 100 for the photovoltaic devices according to the present invention, as illustrated in the drawings, has a cubic box-shaped darkroom 110. An opening portion 112 is disposed on a flat upper surface 111. The opening portion 112 is partially formed at the upper surface of the darkroom 110 in consideration of the dimension of the inspecting object 200. Three cameras 121, 122 and 123 for inspecting the photovoltaic devices as the inspecting object 200 and a moving means thereof are disposed inside the darkroom. It is possible that the moving means is not provided according to the usage. The upper surface 111 other than the opening portion 112 is formed from a shading element to prevent light rays from entering the darkroom 110. It is also possible to make the entire upper surface 111 into the opening portion 112 if the photovoltaic devices as the inspecting object 200 is disposed on the upper surface 111 and then the entire upper surface including the inspecting object 200 is further covered with a shading means. Except the upper surface 111, the other 4 side surfaces and the bottom surface are comprised of shading member. Further, the upper surface 111 is provided with a pair of guide members 114 and 114 to guide the inspecting object 200 during transportation. The distance between the pair of guide members 114 and 114 may be adjusted according to the dimension of the inspecting object 200.

3. Guiding the Inspecting Object 200 for Transportation and Positioning

The guide member 114 is a narrow and long rail having a cross section of a rectangular shape. On the upper surface of the inspecting apparatus 100 according to the present invention, the guide member 114 is disposed in pairs along a direction of transporting the inspecting object 200. On the inner side surface of each guide member 114, plural rollers 115 are disposed. The inspecting object 200 is transported on the rollers 115. The guide members 114 and the plural rollers 115 constitute a support means for supporting the photovoltaic devices panel 30 on the opening portion 112. Therefore, during the transportation and inspection of the inspecting object 200, it is impossible for the inspecting object 200 to fall from the opening portion 112 into the darkroom 110. According to the dimension of the inspecting object 200, the guide member 114 is adjusted through a moving rail 116, feeding screws 117 which are disposed at a transporting-in side and a carrying-out side of the inspecting apparatus and a handle 118. Namely, the feeding screws 117 are comprised of 2 screws, one of which is a right-hand screw and the other one is a left-hand screw. By rotating the handle 118, the guide members 114 and 114 move toward each other or away from each other with the center position therebetween being maintained. Furthermore, the feeding screws 117 in the transporting-in side and the carrying-out side are connected through a cross shaft 113 having bevel gears. When the handle 118 is rotated, the feed screws 117 on both sides can rotate simultaneously through the bevel gears.

One side surface of the guide member 114 is provided with a positioning member 119, which is protruded and withdrawn from the side surface of the guide member 114 by use of an actuator or the like. The transported inspecting object 200 is positioned in the transportation direction by protruding the positioning member 119. The positioning member 119 can not only be configured as being protruded and withdrawn from the inner side of the guide member 114, but also can be configured as ascending and descending from an upper position of the guide member 114, or being rotated downward from the guide member. It is acceptable to dispose a plurality of positioning members 119 along the length direction of the guide member 114 and use an adequate one of the plural positioning members 119 according to the dimension of the inspecting object 200. It is also acceptable that the positioning member 119 is configured to be movable along the length direction of the guide member 114 according to the dimension of the inspecting object 200.

4. Photographing Camera

The inspecting object 200 is made to emit the EL light which is a weak light ray of wavelength between 1,000 nm and 1,300 nm in the darkroom, three photographing cameras 121, 122 and 123 are used to photograph the weak light ray. Therefore, it is necessary to use a CCD camera which has high sensitivity to weak light as the photographing cameras 121, 122 and 123. In the present embodiment, a Si-CCD camera of Model C9299-02 manufactured by Hamamatsu Photonics K. K. is employed.

5. Moving Means for camera

FIG. 2A is a planar view illustrating a configuration of a moving means of the inspecting apparatus; FIG. 2B is a sectional view along A-A line of FIG. 2A; FIG. 2C is a sectional view from the right side along B-B line in FIG. 2A; FIG. 2D is a planar view illustrating allocated parts for each camera in photographing an inspecting object. The cameras 121, 122 and 123 in the darkroom 110 are fixed with the faces thereof upward at a support beam 130 as a support means. The central camera 122 is disposed at the center position between the guide members 114 and 114, and the other cameras 121 and 123 are disposed with an equal distance from the central camera 122. Both ends of the support beam 130 are supported by y axis guide parts 140 and 140, for moving the cameras 121, 122 and 123 along the y axial direction. The support beam 130 can move reciprocally on the y axis guide parts 140 along the y axial direction by a motor 142 and a timing belt 144 disposed on each side. In the aforementioned configuration, the y axis support parts 140 and 140, the motor 142 and the timing belts 144 and 144 constitute the moving means for the cameras 121, 122 and 123. It is possible for the y axis guide parts 140 and 140 to use various types of linear actuators. In the present embodiment, a ball screw is employed.

The driving means is not limited to the aforementioned embodiment where a motor and a ball screw are employed. Various types of linear actuators can be employed.

By controlling the rotations of the motor 142 of the moving means, the cameras 121, 122 and 123 can be moved to an arbitrary position in the y axial direction. As illustrated in FIG. 2D, the inspecting object 200 is divided by two in the y axial direction and three in the axial direction into six allocated parts to be photographed by the cameras 121, 122 and 123 by moving them in the y axial direction for two times denoted by the numerals 1 and 2. The numbers of the cameras, the moving times (photographing times) and the moving direction are given merely for illustration; they can be selected appropriately according to various purposes.

In the present invention, one moving means is sufficient for a plurality of cameras. The plurality of cameras are moved integrally in the same direction for the same distance. The moving means only reciprocates along the y axial direction; therefore, it can be manufactured simple in structure and consequently cheap in price.

6. Shading Means

In the above description, it is described that the shading means covers the entire upper surface 111 of the darkroom. However in the case of the photovoltaic devices panel 30, the back surface member 22 made of resin at the back side is not transparent and has sufficient shading effect. Moreover, the upper surface 111 of the darkroom 110 is comprised of shading members except the opening portion 112. When the inspecting object 200 is larger than the opening portion 112 and the periphery of the opening portion 112 contacts closely the margin 30a of the photovoltaic devices panel 30, the opening portion 112 is covered completely by the inspecting object 200; therefore, the shading means is not necessary.

However, when the inspecting object 200 is smaller than the opening portion 112 or is supported the opening portion 112 without contacting closely thereto, light rays will enter the darkroom 110 from the gap; it is therefore necessary to cover the upper surface of the darkroom with a shading means. As the shading means, for example, a shading cover configured to cover the entire upper surface of the darkroom 100 and the like can be adopted in variety.

7. The Other Devices

Figure 7:
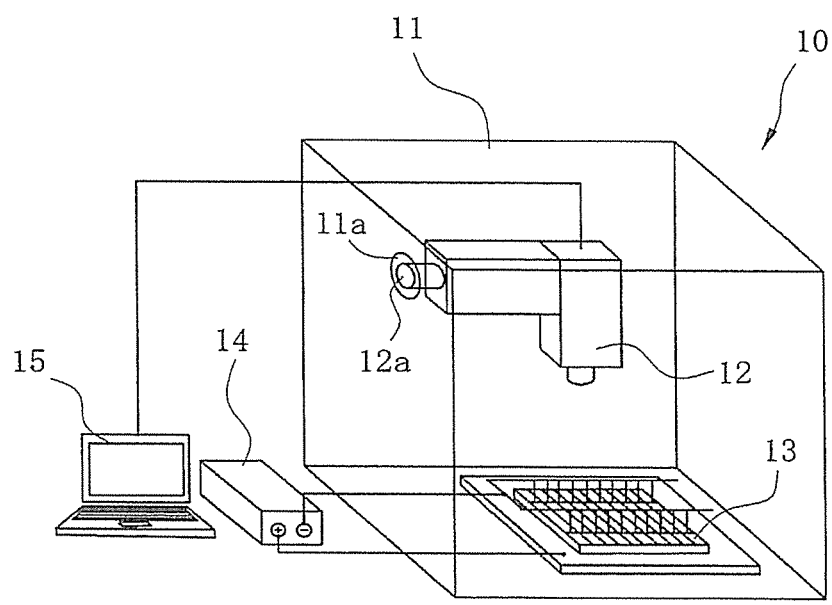
FIG. 7 is a view schematically illustrating a configuration of a conventional inspecting apparatus fro a photovoltaic devices.

In addition to the aforementioned devices, although not illustrated in the drawings, the inspecting apparatus 100 of the present invention is provided with a power source 14 and an image processing apparatus 15 used a computer illustrated in the conventional inspecting apparatus of FIG. 7.

8. Usage of the Inspecting Apparatus

Descriptions will be given on the usage of the inspecting apparatus for the photovoltaic device of the present invention by using the photovoltaic devices panel 30 as an example of the inspecting object 200.

After the photovoltaic devices panel 30 manufactured in a laminator or the like is carried out, it is transported by a conveyor or the like to the immediate front of the inspecting apparatus 100 for the photovoltaic devices of the present invention. The transported photovoltaic devices panel is guided by the pair of guide members 114 and 114 to move on the rollers 115 provided at the inner side of the guide members, and reaches the upper surface of the darkroom 110. Thereafter, the photovoltaic devices panel 30 is positioned in the transportation direction by protruding the positioning member 119 disposed at the side surface of the guide member 114 in a manner that the positioning member 119 is protruded and withdrawn from the side surface thereof by an actuator or the like.

The photovoltaic devices panel 30 as the inspecting object 200 reaches a predetermined position of the darkroom 110, then stops on the opening portion 112 of the darkroom 110 with the transparent glass plate 21 facing downward and is connected with a power source not shown in drawings. Since the inspecting object 200 is smaller than the opening portion 112, light rays will enter the darkroom from the boundary between the inspecting object 200 and the opening portion 112. Therefore, the entire upper surface of the darkroom 110 is covered by a shading means (not shown) from the upper side of the inspecting object 200. A current is applied to the inspecting object 200 from the power source in a forward direction to make the inspecting object 200 emit the EL light, which is photographed by the cameras 121, 122 and 123.

As illustrated in FIG. 2D, each of the cameras 121, 122 and 123 photographs two of the 6 allocated parts on the inspecting object 200. Each of the cameras 121, 122 and 123 moves along the y axial direction by the moving means, and photographs for two photographing times denoted by the numerals 1 and 2 to acquire images for the total 6 allocated parts, respectively. By overlapping the boundary of one image with the boundary of another adjacent image, it is easy to obtain one piece of composite photograph of the photovoltaic devices panel from the image data of each camera.

Since there are provided with a plurality of cameras, it is possible to dispose the cameras closer to the inspecting object 200 to make the height of the darkroom 110 smaller. The number of cameras is not limited to three cameras; generally, a plurality of cameras may be disposed in the darkroom. Furthermore, in the above embodiment, it is described that the cameras are disposed along the x axial direction and moves along the y axial direction; however, on the contrary, it is acceptable that the cameras are disposed along the y axial direction and moves the cameras along the x axial direction.

Since each camera is disposed to photograph the inspecting object 200 closely, it is possible to acquire the image with a perfect resolution. Moreover, since the area of the allocated parts photographed by one camera is small, it is possible to photograph the entire inspecting object 200 in a short time.

By disposing the cameras 121, 122 and 123 with an interval along the x axial direction, for example, and dividing the inspecting object 200 in the length direction into three equal parts so that each camera can photograph one part of the three parts to obtain the entire inspecting object 200 for one photographing time; the moving means is not necessary. If the moving means is not needed, the cameras 121, 122 and 123 can be fixed at the bottom of the darkroom 110 to make photographing.

In the embodiment mentioned above, the inspecting object 200 is the photovoltaic devices panel 30; however, it is not limited thereto. The inspecting object 200 may be one piece of the photovoltaic cell 28, the photovoltaic string 25 which is formed by connecting plural photovoltaic cells 28 with the lead wires 29.

The image processing apparatus analyzes those portions which emit no EL light from the image of each photovoltaic cell 28 to determine whether the respective photovoltaic cell 28 is passed or not. Whether the photovoltaic devices panel 30 as a whole is passed or not is determined on the basis of the analysis results for all photovoltaic cells 28.

The photographing by the cameras 121, 122 and 123 may be performed by photographing each piece of the photovoltaic cells, increasing the number of the cameras, or increasing the moving times of the cameras, or may be performed by photographing several pieces of the photovoltaic cells at one time.

9. Embodiment Employed with a Reflective Plate

FIG. 3A is a planar view illustrating an embodiment of the present invention where the darkroom is further miniaturized; FIG. 3B is a sectional view along C-C line of FIG. 3A; and FIG. 3C is a sectional view from the right side along D-D line in FIG. 3A. In the darkroom, the support beam 130 is disposed as the support means, and three cameras 121, 122 and 123 are supported by the support beam 130 horizontally. Both ends of the support beam 130 are supported by the x axis guide parts 140 and 140, respectively, and the cameras 121, 122 and 123 reciprocates as a whole by the motor 142 and the timing belts 144 and 144 for the same distance along the y axial direction. The configuration above is the same as the embodiment illustrated in FIG. 2.

In the embodiment of the present invention, reflective plates 131, 132 and 133 made of aluminum or the like are disposed in front of the cameras, respectively, in a way of being oblique to the opening portion 112. Each of the reflective plates 131, 132 and 133 is configured to be integral to each of the cameras 121, 122 and 123, respectively and reciprocate along the y axial direction together with the cameras 121, 122 and 123. Each camera photographs reflection rays of an allocated part on the inspecting object reflected by each reflective plate as a partial image of the inspecting object 200, and photographs all allocated parts according to repeated movements. The entire image of the inspecting object 200 is acquired by integrating all images from each camera. According to such configuration, the distance from each camera to the inspecting object 200 as the photographing object can be maintained constant.

Although not shown in the drawings, it is acceptable to fix the cameras at one end of the darkroom facing to the lateral direction and to move the reflective plates only by the moving means.

10. Embodiment for Rocking the Cameras

FIG. 4A is a planar view illustrating an embodiment of a moving means for rocking the camera; FIG. 4B is a sectional view along E-E line in FIG. 4A; FIG. 4C is a sectional view from the right side along F-F line in FIG. 4A; and FIG. 4D is a planar view illustrating allocated parts for each camera in photographing the inspecting object. In the present embodiment, a transparent plate 108 is installed to an opening portion at the upper surface of the darkroom 110. However, it is acceptable that a transparent plate 108 is not installed to an opening portion at the upper surface of the darkroom 110 as the aforementioned embodiment. On the other hand, it is also acceptable to obdurate the opening portion 112 with the transparent plate 108. The transparent plate 108 is made of glass or synthetic resin such as acryl resin. It is acceptable to install the transparent plate 108 to the opening portion at the upper surface of the darkroom 110 in the embodiments illustrated in FIG. 2 and FIG. 3.

Installation of the transparent plate 108 to the opening portion 112 can prevent dust or the like from entering the darkroom 110, and consequently, preventing the darkroom 110 and the camera from being polluted. On the other hand, since the EL light emitted from the photovoltaic devices panel is weak, it will be further attenuated if the transparent plate 108 is installed, which makes the photovoltaic devices panel more difficult to be photographed; therefore, in some cases, it is preferred that the transparent plate 108 is not installed.

In the present embodiment, four cameras 121, 122, 123 and 124 are disposed along the x axial direction. The 4 cameras are fixed at the support beam 150 as the support means. Both ends of the support beam 150 are disposed with a conventional rocking means 151, respectively, to rock the cameras 121, 122, 123 and 124 in a range from 123' to 123" as illustrated in FIG. 4C.

As illustrated in FIG. 4D, the cameras 121, 122, 123 and 124 photographs the allocated parts divided in parallel to the y axis. First, the cameras are directed toward the center to photograph the four allocated parts denoted by the numeral 1 in the central portion in FIG. 4D. Subsequently, four cameras are rocked by the rocking means 150 to the position of 123" in FIG. 4C and photographs the four allocated parts denoted by the numeral 2; and thereafter, four cameras are rocked to the position of 123' in FIG. 4C and photographs the four allocated parts denoted by the numeral 3. Accordingly, the inspecting object 200 can be photographed by a total of twelve allocated parts for the inspection. By overlapping the boundary of one image with the boundary of another adjacent image to join the entire image, it is easy to obtain the entire image of the inspecting object 200. The rocking means 151 is simple in structure and can be manufactured cheap in price.

11. Embodiment for Rocking Only the Reflective Plate

FIG. 5A is a planar view illustrating an embodiment where only the reflective plate is rocked; FIG. 5B is a sectional view along G-G line of FIG. 5A; and FIG. 5C is a sectional view from the right side along H-H line of FIG. 5A. The support beam 150 is disposed in the darkroom as the support means, and four reflective plates 131, 132, 133 and 134 are supported thereon. The reflective plates 131, 132, 133 and 134 are rocked by the rocking means 151 disposed at both ends of the support beam 150, respectively, in a range from 133' to 133" as illustrated in FIG. 5C.

As illustrated in FIG. 5C, the cameras 121, 122, 123 and 124 are fixed at the right side of the bottom or the like of the darkroom, facing to the lateral direction. The reflective plates 131, 132, 133 and 134 are configured to rotate integrally to the same direction at the same angle.

According to the mentioned configuration, since the cameras 121, 122, 123 and 124 are fixed and only the light-weighted reflective plates 131, 132, 133 and 134 are rocked, the moving portion can be made light and cheap.

As many apparently widely different embodiments of the present invention can be made without departing from the spirit and scope thereof, it is to be understood that the invention is not limited to the specific embodiments thereof except as defined in the appended claims.

What is claimed is:

1. An inspecting apparatus for a photovoltaic devices, wherein the inspecting apparatus inspects a photovoltaic devices by applying a current to an inspecting object, which is the photovoltaic devices, in a forward direction to make the inspecting object emit an electro-luminescence light and the emitted electro-luminescence light is photographed and defects of the photovoltaic devices are inspected from a photographed image, the inspecting apparatus comprising:
 a darkroom provided with an upper surface having an opening portion;
 a support means provided at the upper surface of the darkroom to support the photovoltaic devices as the inspecting object on the opening portion;
 a plurality of cameras disposed inside the darkroom to photograph the inspecting object, and
 a shading means covering the inspecting object, the opening portion, and the support means;
 wherein the inspecting object is divided into a plurality of allocated parts, the plurality of cameras are respectively disposed with respect to the plurality of allocated parts, and each of the allocated parts is photographed by each of the plurality of cameras in a manner that a boundary of an image with a boundary of another adjacent image are overlapped, so that an entire image of the photovoltaic devices is formed.

2. The inspecting apparatus for a photovoltaic devices according to claim 1, wherein a moving means is provided in the darkroom to move the plurality of cameras.

3. The inspecting apparatus for a photovoltaic devices according to claim 2, wherein the moving means comprises a support member for fixing the plurality of cameras, and the moving means reciprocates the support member linearly.

4. The inspecting apparatus for a photovoltaic devices according to claim 2, wherein each of the plurality of cameras is provided with a reflective plate to photograph each of the allocated parts.

5. The inspecting apparatus for a photovoltaic devices according to claim 4, wherein the moving means moves the reflective plate together with the camera.

6. The inspecting apparatus for a photovoltaic devices according to claim 1, wherein a rocking means is provided in the darkroom to rock each of the plurality of cameras for photographing the allocated part.

7. The inspecting apparatus for a photovoltaic devices according to claim 1, wherein each of the plurality of cameras is provided with a reflective plate to photograph the allocated part and a rocking means for rocking the reflective plate.

8. The inspecting apparatus for a photovoltaic devices according to claim 1, wherein the opening portion is obturated by a transparent plate.

* * * * *